United States Patent [19]

Harless

[11] Patent Number: 4,769,171

[45] Date of Patent: Sep. 6, 1988

[54] LIQUID EAR CLEANSING COMPOSITION

[75] Inventor: Stanley J. Harless, Omaha, Nebr.

[73] Assignee: Harlmen, Inc., Omaha, Nebr.

[21] Appl. No.: 47,477

[22] Filed: May 11, 1987

[51] Int. Cl.$^4$ .................... C11D 3/44; C11D 7/26
[52] U.S. Cl. .................... 252/142; 252/106; 252/136; 252/139; 252/143; 252/162; 252/170; 252/174.16; 252/DIG. 5; 252/DIG. 14
[58] Field of Search .......... 252/136, 139, DIG. 5, 252/DIG. 1, 143, 162, 170, 174.16, 106, DIG. 14

[56] References Cited

U.S. PATENT DOCUMENTS

| | | | |
|---|---|---|---|
| 3,925,229 | 12/1975 | Bolsing | 252/136 |
| 4,169,065 | 9/1979 | Robertson | 252/104 |
| 4,336,152 | 6/1982 | Like et al. | 252/106 |
| 4,358,389 | 11/1982 | Konig-Lumer et al. | 252/70 |
| 4,372,788 | 2/1983 | Lancz | 134/4 |
| 4,495,079 | 1/1985 | Good | 252/106 |
| 4,501,680 | 2/1985 | Aszman et al. | 252/142 |
| 4,612,058 | 9/1986 | Geke et al. | 134/38 |
| 4,619,711 | 10/1986 | Olbrueck et al. | 134/38 |

OTHER PUBLICATIONS

Advanced Organic Chemistry, by Jerry March, McGraw-Hill, 1977 p. 923 Reactions.
"Facts and Comparisons: Drug Information" 1980 ed., A. Kastrup, editor, Facts and Comparisons, Inc., St. Louis, pp. 1518–1532.
"Otic Products, In: Handbook of Non-Prescription Drugs." 8th edition, K. O. Miller, editor, American Pharmaceutical Assn. Washington, chapter 20, pp. 419–435.

Primary Examiner—Paul Lieberman
Assistant Examiner—Ronald A. Krasnow
Attorney, Agent, or Firm—Larson and Taylor

[57] ABSTRACT

A liquid ear cleansing composition for topical application to ears is disclosed. The composition has a pH of about 1.9 to about 2.7 and includes an acid buffer system. The composition also includes propylene glycol as a solvent, a thickening agent and a surface active agent. The ear cleansing composition is effective against yeast infections in dissolving ear wax and as a carrier material for topical application of antibiotics and steroids.

10 Claims, No Drawings

4,769,171

LIQUID EAR CLEANSING COMPOSITION

FIELD OF THE INVENTION

The present invention relates to a liquid ear cleansing composition. More particularly, the present invention relates to a liquid ear cleansing composition comprising a buffered acid solution for eliminating yeast infections and dissolving ear wax.

BACKGROUND OF THE INVENTION

Yeast infections are a major problem among animals and humans and often develop as a result of administration of antibiotics given to treat other types of unrelated infections. Yeast infections are known to thrive in the environment that is created by administration of antibiotics.

Yeast infections commonly occur in the ears or other orifices of the body and are presently treated by the topical application of a composition known to be harmful to the yeast organism. One such composition used to treat yeast infections is a mixture of vinegar and water, the active ingredient of which is acetic acid. It has been found that an acidic environments of this type tend to eliminate yeast infections.

There are several disadvantages, however, with present methods of treatment for yeast infections. For instance, vinegar and water solutions are often too runny and thus will not remain in contact with the area to which they are applied. Many animals will shake vinegar and water solutions out of their ears and off of their bodies soon after application. Another problem with the vinegar and water solution treatment is that there is poor control of the pH of the solution. A pH which is too low will cause irritation of the ear and other parts of the body. On the other hand, a pH which is too high will not affect the yeast organism and, therefore, will not accomplish the desired results. Accordingly, control of the pH of the treatment composition is important to the safety and effectiveness of the composition.

Another disadvantage of the present methods for treating yeast infections in ears is that the present compositions do not dissolve ear wax. It is desirable in the treatment of yeast infections in ears that the treating composition not only eliminate the yeast organism but also dissolve wax present in the ear so as to clean the ear passage.

Cleaning compositions employing phosphoric acid and a surface active agent are described in U.S. Pat. Nos. 3,793,221, 3,832,234 and 3,645,790. However, these cleaning compositions incorporate additional ingredients and are indicated for use as metal cleaners. No indication of topical application to humans or animals is disclosed.

U.S. Pat. No. 4,336,152, issued on June 22, 1982, discloses a disinfectant cleanser containing a surface active agent, a lower aliphatic alcohol and a phosphate builder. This composition exhibits a reduced eye irritancy as well as germicidal activity. However, there is no indication that the composition contains a buffer system or that it can be topically applied. Moreover, the composition does not include phosphoric acid.

U.S. Pat. No. 2,689,814, issued on Sept. 21, 1954, discloses a germicidal composition including a surface active agent in a propylene glycol solution. However, this compostion neither contains phosphoric acid nor a buffer system.

U.S. Pat. No. 4,384,003 issued on May 17, 1983 discloses a suppository including a surface active agent, a thickener and vegetable oil. This suppository is in the form of a gel and may be used as a carrier for spermicide. The composition is not indicated for ear cleaning and contains neither phosphoric acid, propylene glycol nor a buffer system.

U.S. Pat. No. 4,181,622, issued on Jan. 1, 1980, discloses a cleaning composition for removal of marine vegetation from water-immersed surfaces. The composition includes phosphoric acid and an alcohol in aqueous solution. There is no disclosure of a surface active agent, a thickener or the presence of a buffer system. Also, the composition is not indicated for ear cleaning.

Accordingly, it is the primary object of the present invention to provide a composition for topical treatment of yeast infections which offers good pH control of the composition and the treated area.

It is another object of the present invention to provide a composition for the topical treatment of yeast infections which is of sufficient viscosity to maintain the composition in contact with the yeast infection.

A further object of the present invention is to provide a buffered acid solution for topical treatment of yeast infections.

Yet another object of the present invention is to provide a composition for topical application to yeast infections which exhibits antibiotic and antifungal activity as well.

A still further object of the present invention is to provide a composition for the topical treatment of yeast infections which also helps to dissolve ear wax.

Another object of the invention is to provide a composition for the topical treatment of yeast infections which is not harmful to the eyes or delicate membranes of the body.

It is an even further object of the present invention to provide a composition for the topical treatment of yeast infections which is also useful as a carrier material for topical application of antibiotics or steroids.

These and other objects of the present invention will be apparent to one of ordinary skill in the art from the summary and detailed description which follows.

SUMMARY OF THE INVENTION

The present invention relates to a buffered acid solution which is useful as an ear cleansing product which comprises a propylene glycol solvent, an amount of an acid sufficient to provide a buffered acid solution having a pH of about 1.9 to about 2.7, a thickening agent, and a surface active agent.

In another embodiment, the present invention also relates to a method of cleaning ears comprising the step of applying a sufficient amount of a liquid buffered acid solution to an ear to clean the ear, the solution comprising propylene glycol solvent, an amount of an acid sufficient to provide a buffered acid solution having a pH of about 1.9 to about 2.7, a thickener, and a surface active agent.

DETAILED DESCRIPTION OF THE PREFERRED EMBODIMENTS

The liquid ear cleansing composition of the present invention includes a propylene glycol solvent, an amount of an acid sufficient to provide a buffered acid solution having a pH of about 1.9 to about 2.7, a thickener, and a surface active agent. This composition is designed to be topically applied to an infected area in order to eliminate yeast infections, as well as accomplish other objectives. Some of the other objectives include dissolving ear wax, if the composition is applied to an ear; or the composition may be used as a carrier material for topical application of antibiotics or steroids.

The solvent used in the present invention is preferably propylene glycol. Propylene glycol is an especially useful solvent for several reasons. First, propylene glycol is an approved solvent for drugs, cosmetics, lotions and ointments. In addition, it has a low index of toxicity if accidentally taken internally. Also, propylene glycol is a nonionic cleansing compound that is water-soluble, and consequently does not leave greasy the area to which it is applied. Finally, literature indicates propylene glycol is an effective topical treatment for a skin rash caused by *Pityrosporum orbiculares* and *Pityrosporum ovali*. Propylene glycol is also an effective treatment for *Pityrosporum pachydermatis* in the canine and feline ear. For these reasons propylene glycol is an ideal solvent for use in the present ear cleansing composition. The solvent preferably comprises from about 50% to about 85% of the present composition.

One of the more important features of the present composition is the buffer system included therein. In the treatment of yeast infections it is important to topically apply a composition having a pH of about 1.9 to about 2.7. Compositions in this pH range will effectively eliminate the yeast organism. However, compositions having a pH of greater than 2.7 will not have a substantial effect on the yeast organism. On the other hand, compositions having a pH of less than 1.9 are often irritating to the skin and membranes and therefore undesirable. As a result, it is important to maintain the pH of the ear cleansing composition at about 1.9 to about 2.7. An even more preferred pH range is about 2.3 to about 2.5.

Excellent control of the pH of the ear cleansing composition is obtained by incorporating a buffer system in the composition. The buffer system maintains the pH of the cleansing composition at the desired level during storage of the composition. Moreover, the buffer system effectively maintains the pH of the composition after it is topically applied and exposed to the environment. This can be crucial since a pH of about 1.9 to about 2.7 is required to effectively eliminate yeast infections. Also, maintaining the pH at a level greater than about 1.9 is important because lower pH's will result in harm to the area being treated.

Any acid which is soluble in propylene glycol and which creates a buffer system in solution may be used in the ear cleansing composition of the present invention. The preferred acid is phosphoric acid due to its excellent properties and it effectiveness as a buffer system. In addition, phosphoric acid is a strong enough acid to generate the required pH for eliminating yeast infections. The acid preferably will comprise from about 2% to about 8% of the composition.

The composition of the present invention also includes a thickener for adjusting the viscosity of the solution. It is desirable that compositions used for topical applications be of sufficient viscosity to remain on the skin where they are applied. Buffered acid solutions generally do not have the required viscosity for topical application. As a result they are prone to run off the skin where they are applied, or may be shaken off by the animal to which they are applied. Therefore a thickener is incorporated in the solution to raise the viscosity of the solution and impart the necessary properties for topical application. The thickener preferably comprises from about 2% to about 10% of the composition.

The preferred thickening agent of the present invention is carboxymethylcellulose. Carboxymethylcellulose is useful as a thickening agent because it is not absorbed, and because it is hydrophilic. Enough carboxymethylcellulose is incorporated in the composition to give the composition the desired viscosity for topical application. A syrupy, oily or pasty consistency is sufficient for topical application since the composition should be capable of flowing down into an ear. Another advantage of using carboxymethylcellulose is that it will have no adverse reaction if accidentally instilled into the eye since it is hydrophilic. Carboxymethylcellulose also aids in absorbing excess moisture in the area of application since it is hydrophilic. Other standard thickening agents may be used in the composition of the present invention as long as they are not harmful to the skin or eyes.

The composition of the present invention also preferably includes a surface active agent. The surface active agent helps the composition of the present invention to penetrate the walls of the yeast organism and thereby effectively eliminate these organisms. The surface active agent also helps to dissolve ear wax. The surface active agent preferably comprises from about 0.25% to about 2.5% of the composition.

Any surface active agent known to one of ordinary skill in the art may be used in the present invention as long as it is not harmful when topically applied to the skin. The preferred surface active agent for use in the present invention is a non-ionic surfactant of the ethoxylated monohydric alcohol type such as Triton X.

The composition of the invention may optionally include a base for adjustment of the pH into the prefered pH range. Alkali metal hydroxides may be used for this purpose and potassium hydroxide is the preferred base due to its ionization potential.

The composition of the present invention is useful as a topical ear cleansing composition. This composition will dissolve ear wax and absorb excess moisture present in the ear. Further, the composition will lower the pH of the ear canal and maintain this lower pH through the action of the buffer system to thereby create an environment which is fatal to the yeast organism. The composition is designed to be topically applied in an amount sufficient to provide cleaning of the ear, as well as to lower the pH of the ear to about 1.9 to about 2.7 and more preferably to about 2.3 to about 2.5. The composition may be applied by spraying, pouring, or any other method of direct application to the infected area. Approximately 0.1 ml to about 2.0 ml must be applied to an ear in order to successfully treat a yeast infection. This amount may vary depending on the size of the ear. Application of more than 2.0 ml is possible but usually results in an overflow of the ear and hence no additional activity.

The composition of the present invention may also be used as a liquid carrier material for topical application of other compositions such as antibiotics and steroids. To use the composition of the present invention in this manner, one would simply incorporate a steroidal or antibiotic composition into the solution of the present invention in an amount sufficient to provide the desired activity. The only limitation would be that the antibiotic or steroidal material would have to be soluble in propylene glycol.

The following illustrative examples are provided to illustrate a specific embodiment of the present invention.

EXAMPLE 1

TABLE 1

| Ingredient | Amount |
| --- | --- |
| Propylene Glycol | 750.0 cc. |
| Carboxymethylcellulose 8,000 | 50.0 g. |
| Triton X 100 | 5.0 cc. |
| Phosphoric Acid | 30.0 cc. |

The four ingredients listed in Table 1 above were mixed together and the pH was adjusted to 2.4 with concentrated potassium hydroxide solution. The resulting composition was topically applied to the ears of several canines and was found to eliminate yeast infections and dissolve ear wax.

EXAMPLE 2

The composition of Example 1 was tested against a vinegar and water solution in comparative tests. It was found that the composition of Example 1 was easier to apply, and exhibited superior activity against yeast organisms.

It is to be understood that the foregoing examples have been given for illustrative purposes only and should not be interpreted as limiting the present invention, the scope of which should be determined from the claims appended hereto.

What is claimed is:

1. A buffered acid solution which is useful as an ear cleansing product comprising:
   propylene glycol solvent;
   an acid capable of dissociating in propylene glycol;
   a sufficient amount of a thickening agent to adjust the viscosity of the solution for topical application; and
   an amount of a surface active agent to make up from about 0.25% to about 2.5% of the solution;
   the buffered acid solution having a pH of about 1.9 to about 2.7.

2. A composition as claimed in claim 1 further including a base.

3. A composition as claimed in claim 2 wherein said base comprises potassium hydroxide.

4. A composition as claimed in claim 2 wherein said acid comprises phosphoric acid.

5. A composition as claimed in claim 2 wherein said solution has a pH of about 2.3 to about 2.5.

6. A method of cleaning ears comprising the step of applying a sufficient amount of liquid buffered acid solution to an ear to clean the ear, said solution comprising:
   propylene glycol solvent;
   an acid capable of dissociating in propylene glycol;
   a sufficient amount of a thickening agent to adjust the viscosity of the solution for topical application; and
   an amount of a surface active agent to make up from about 0.25% to about 2.5% of the solution;
   the buffered acid solution having a pH of about 1.9 to about 2.7.

7. A method as claimed in claim 6 wherein said composition further comprises a base.

8. A method as claimed in claim 7 wherein said base comprises potassium hydroxide.

9. A method as claimed in claim 7 wherein said acid comprises phosphoric acid.

10. A method as claimed in claim 7 wherein said solution has a pH of about 2.3 to about 2.5.

* * * * *